US012539186B2

(12) United States Patent
Hoegerle et al.

(10) Patent No.: US 12,539,186 B2
(45) Date of Patent: Feb. 3, 2026

(54) ELECTROMECHANICAL STERILE SEPARATION

(71) Applicant: Aesculap AG, Tuttlingen (DE)

(72) Inventors: Roland-Alois Hoegerle, Tuttlingen (DE); Thorsten Ketterer, Constance (DE)

(73) Assignee: Aesculap AG, Tuttlingen (DE)

( * ) Notice: Subject to any disclaimer, the term of this patent is extended or adjusted under 35 U.S.C. 154(b) by 467 days.

(21) Appl. No.: 18/012,323

(22) PCT Filed: Jun. 25, 2021

(86) PCT No.: PCT/EP2021/067533

§ 371 (c)(1),
(2) Date: May 11, 2023

(87) PCT Pub. No.: WO2021/260191

PCT Pub. Date: Dec. 30, 2021

(65) Prior Publication Data

US 2023/0255713 A1 Aug. 17, 2023

(30) Foreign Application Priority Data

Jun. 25, 2020 (DE) ..................... 10 2020 116 769.5

(51) Int. Cl.
*H01R 13/639* (2006.01)
*A61B 46/10* (2016.01)

(52) U.S. Cl.
CPC ........... *A61B 46/10* (2016.02); *H01R 13/639* (2013.01); *H01R 2201/12* (2013.01)

(58) Field of Classification Search
CPC ... A61B 46/10; H01R 13/639; H01R 2201/12
(Continued)

(56) References Cited

U.S. PATENT DOCUMENTS

2003/0216723 A1 11/2003 Shinmura et al.
2016/0058513 A1 3/2016 Giorgi
(Continued)

FOREIGN PATENT DOCUMENTS

DE 202007002332 U1 5/2007
DE 102015207953 A1 11/2016
(Continued)

OTHER PUBLICATIONS

Communication received in European Application No. 21 737 4032-1113 dated Jan. 28, 2025, with translation, 14 pages.
(Continued)

*Primary Examiner* — Tulsidas C Patel
(74) *Attorney, Agent, or Firm* — Christopher A. Rothe; CM Law

(57) ABSTRACT

A sterility separation element can be arranged between plug connectors of a plug connection/electro-mechanical lock to provide sterility separation of the plug connectors. The plug connection/electro-mechanical lock has at least one electrical contact pin that penetrates the sterility separation element such that the sterility separation element fits directly to the electrical contact pin over its entire circumference in a germ-tight manner. The electrical contact pin has two free pin ends configured to come into electro-mechanical or electroconductive plug contact with corresponding electrical plug sockets of at least two lines to be connected.

20 Claims, 3 Drawing Sheets

(58) Field of Classification Search
USPC .......... 439/577; 128/853, 854, 856; 600/102
See application file for complete search history.

(56) References Cited

U.S. PATENT DOCUMENTS

| | | | | |
|---|---|---|---|---|
| 2016/0242861 A1* | 8/2016 | Flatt | A61B 90/40 | |
| 2018/0049833 A1 | 2/2018 | Shelton, IV et al. | | |
| 2018/0145443 A1 | 5/2018 | Andreason et al. | | |
| 2019/0290379 A1 | 9/2019 | Flatt et al. | | |
| 2020/0069383 A1 | 3/2020 | Betsugi et al. | | |
| 2020/0170724 A1* | 6/2020 | Flatt et al. | A61B 34/30 | 74/490.05 |

FOREIGN PATENT DOCUMENTS

| | | | |
|---|---|---|---|
| JP | H0767885 A | 3/1995 | |
| JP | 2003325543 A | 11/2003 | |
| WO | 2016134266 A1 | 8/2016 | |

OTHER PUBLICATIONS

Office Action received in Japanese Application No. 2022-580152 dated Dec. 11, 2024, with translation, 7 pages.
Search Report received in German Application No. 10 2020 116 769.5 dated Mar. 29, 2021, with translation, 11 pages.
Search Report received in International Application No. PCT/EP2021/067533 dated Oct. 6, 2021, with translation, 6 pages.
Written Opinion received in International Application No. PCT/EP2021/067533 dated Oct. 6, 2021, with translation, 13 pages.

* cited by examiner

ELECTROMECHANICAL STERILE SEPARATION

CROSS-REFERENCE TO RELATED APPLICATION(S)

This application is the United States national stage entry of International Application No. PCT/EP2021/067533, filed Jun. 25, 2021, and claims priority to German Application No. 10 2020 116 769.5, filed Jun. 25, 2020. The contents of International Application No. PCT/EP2021/067533 and German Application No. 10 2020 116 769.5 are incorporated by to reference herein in their entireties.

FIELD

The disclosure relates to a sterility barrier with a covering or separation element, e.g. a sheet or foil (also referred to as a drape) and an electro-mechanical, germ-tight lock integrated or integrable/mountable therein for transmission of electrical energy and/or electrical control signals from a non-sterile-side wiring to a sterile-side wiring.

BACKGROUND

Increasing digitization in the operating room is leading to an increasing integration of electronics and software in electrically driven surgical motor systems. Since electronic elements can only be reprocessed with great effort and not without limitations, the basic aim is to offer or separate surgical drives, for example, in a sterile area (materials reprocessable without limitations and operatable by the surgeon without limitations) and in a non-sterile area (materials that are critical for reprocessing and must not be touched by the surgeon). One advantage of this concept is that the surgeon has to handle the smallest possible mass (volume), since essential parts of the surgical drives are shifted to the non-sterile area. These two areas (sterile area/non-sterile area) must then, on the one hand, be contacted electromechanically before the operation and, on the other hand, alternately decontacted/disconnected during the operation and contacted again with other sterile areas. Ideally, this work is to be performed by sterile personnel at the operating table, in compliance with sterility requirements. This requires a sterility separation concept that is adapted to the current requirements of surgical hygiene and can be operated securely.

It is already known, for example, to attach a so-called protective shield to a sterile motor cable. The protective shield is positioned such that it reduces the risk of contact with non-sterile components during a connection/plug process or, respectively, the plugging of the motor cable into the non-sterile control unit. This so-called protective shield is also called a sterility protection cap.

However, a significant disadvantage thereof is that after a single connecting/plugging, the motor cable is, at least in the area of its connector, contaminated and it is no longer possible to disconnect/unplug the cable and return it to a sterile instrument table within the sterile area. This prevents different drives from being used for different surgical steps during an operation.

Furthermore, in the state of the art there are so-called sterility barriers in form of covering or separation sheets which separate the sterile area from the non-sterile area and are equipped with an interface or port, respectively, via which supply lines can be passed. For this purpose, such an interface has a number of flaps which can be opened and closed such as to create corresponding passages as required.

US 2018/0 145 443 A1 discloses an electrical connector which is associated with an electromagnetic tracking device movable and trackable within a patient's body. Thereby, in a multipart electrical (plug) connector system used in a medical environment, a first section of the connector system is arranged to pierce a formable sterility barrier, for example of a fibrous material, this being done while coupling a first part of the connector system to a second part of the connector system. However, it is disadvantageous here, as can be understood especially from FIGS. 9, 11A as well as 11E US 2018/0 145 443 A1, that with the proposed piercing the path for germs is (locally) free at the respective spot. As a result of unhindered germination across the pierced hole, any sterility that may have previously existed is naturally impaired or terminated.

US 2018/0 049 833 A1 discloses a sterile barrier for use with a surgical robotic system. The sterile barrier may include a housing configured to mate with a tool driver mated to a robotic arm and to removably receive a surgical tool. The housing of the sterile barrier has a sterile flexible fabric extending therefrom such that the housing and the flexible fabric are formed in more than one plane and define a sterile side on which the surgical tool is arranged and a non-sterile side on which the tool is arranged. The housing may have at least one electrical pin-shaped contact configured to operably mate with at least one complementary electrical contact at at least one of the tool driver and of the robotic arm. Thereby, the fabric is formed with prefabricated openings arranged or, respectively, configured to pass the electrical pin-shaped contacts therethrough, respectively.

US 2016/0 058 513 A1 discloses another sterility barrier known in the prior art. Thereby, a surgical system includes a first element with a seat which removably receives a surgical instrument for operational use thereof. At least one of two connectors provided with electrical contacts for engagement in the other connector is adapted to be controllably movable between a first retracted rest position and a second advanced position for the electrical connection together with the other connector.

Furthermore, DE 20 2007 002 332 U1 of the present applicant discloses a medical sterile cover, wherein a plug contact is inserted into the respective plug socket through respective openings provided in the cover. Thereby, firm adhesions are proposed for the purpose of sealing.

SUMMARY

It is therefore the object of the disclosure to avoid or at least mitigate the disadvantages of the prior art. Especially, an interface, for example an electromechanical interface, at an operating table for repeated adaptation/separation of sterile application parts to non-sterile operating parts should be secure, hygienic and/or simply thus cost-effective.

The accompanying FIG. 4 shows a general arrangement of a sterile and non-sterile area which are separated by a sterility barrier and as may be provided for the present disclosure.

For example, a robot 100 including actuators or a holding device is located in a non-sterile area U, which is shielded from the surrounding sterile area S by means of a drape 101. The drape has at least two locks/openings 102, 103, of which the one lock 102 is configured as a passage opening for a holding arm of the robot 100 and the other lock 103 is configured to connect a sterile cable section 104 in the sterile area S to a non-sterile cable section within the non-sterile area U (not shown). For this purpose, a connector device 105 is provided. In this case, the cable in the sterile area S is connected to a control 106, for example, for controlling the robot 100.

Other basic application examples include e.g. contacting of a drive motor in the sterile area to a control module or a robot arm in the non-sterile area, and the like.

The core idea of the present disclosure essentially consists in providing a simple sterility separation element (sterility barrier), for example in form of a sheet, foil or drape, as well as an electro-mechanical lock/coupling, with at least one contact pin which is arranged and configured such that it can be inserted/pierced/is pierced into the sterility separation element from one side thereof in the manner of a mandrel, such that it projects from the other side of the sterility separation element. As a result of this, the at least one contact pin is surrounded (immediately/directly) in a germ-tight manner by the sterility separation element or, respectively, the sterility separation element fits in a germ-tight manner to the at least one contact pin all around, wherein the contact pin can be contacted at at least one end/end section by a line, for example by means of a plug socket or a plug.

It should already be noted at this point that the at least one contact pin may have two rod/pin ends which are essentially uniform/identical to one another such that two sockets which are uniform/identical to one another having or consisting of corresponding socket-/sleeve-shaped contact elements can be plugged on both sides. Alternatively, however, it is also conceivable to form the at least one contact pin with (two) mutually different pin ends, especially such that the one end, preferably on the non-sterile side of the sterility separation element, is formed as a (small-diameter) pin and the other end, preferably on the sterile side of the sterility separation element, is formed as a (large-diameter) sleeve/plug socket. In this way, on the one (non-sterile) side, a type of socket/plug socket with a (large-diameter) sleeve-shaped contact pin and, on the other (sterile) side, a type of plug/insertion pin with a (small-diameter) pin shape can be plugged into/onto the contact pin penetrating the sterility separation element. The latter offers the advantage that, for example, electrical medical instruments on the sterile side, which are usually equipped with electrical cables and cable plugs (with pin-shaped electrical contacts) fixed thereto, can be electrically coupled to the at least one contact pin (or, respectively, its sleeve-shaped pin end) without additional (intermediate) adapters. The same also applies to so-called extension cables on the non-sterile side, whose, respectively, one end socket with at least one sleeve-shaped contact pin can also be electrically coupled without adapters to the pin end, formed there as a pin, of the at least one contact pin inserted into the sterility separation element.

Preferably (alternatively or cumulatively), the at least one contact pin is held on the one side of the sterility separation element in/by a first housing which either forms a receiving shaft for a plug socket and/or plug or from which at least one line is led out which is fixed to the at least one contact pin. It should also be noted here that a same type of receiving shaft or plug socket does not necessarily have to be arranged on both sides of the sterility separation element, but that it may be provided to arrange a plug on the one, preferably non-sterile side of the sterility separation element and a plug socket on the other, preferably sterile side.

Further preferably (alternatively or cumulatively), a second housing is provided on the other side of the sterility separation element, which is configured to be pressed against the first housing via the sterility separation element (as sterile intermediate layer), wherein thus the at least one contact pin pierces the sterility separation element and projects into the interior of the second housing. The second housing may thereby preferably be formed as a receiving shaft, such that a further plug socket or plug can be inserted into the second housing and contacted with the at least one contact pin; and further preferably holds the second housing at the contact pin and thus at the first housing.

Such a design is particularly simple, inexpensive and yet secure, and thus especially suitable for one-way sterility sheets.

In other words, according to the disclosure, a flat, preferably flexible sterility element for sterility separation is provided. The sterility separation element is provided or formed to be arranged between first and second plug connectors/housings of a plug connection/electro-mechanical lock, or to be fitted therebetween; and is thus provided or formed to provide or effect sterility separation of the plug connectors.

The plug connection may preferably be a force-locking and/or form-fit connection. When connecting the first and second plug connectors/housings, the sterility separation element may preferably be located between the plug connectors such that the sterility separation element adapts quasi by itself to a geometric shape of the plug connection between the plug connectors.

The term "sterility separation" shall be construed herein to mean, especially, that sterile elements are separated from non-sterile elements such that the sterile element is not contaminated at least at provided points of contact or, respectively, at the points provided for manual operation/touching.

Advantageous embodiments are explained in more detail below.

For example, the sterility separation element may be foldable and/or flexible. The sterility separation element may also be provided for one-time use (English: single-use), for example as a disposable article. In this way, a secure and hygienic sterility separation means can be provided in a simple manner.

The plug connection may be an electrical plug connection. One of the plug connectors of the plug connection may be male (contact pin), and the other of the plug connectors of the plug connection may be female (plug socket).

The sterility separation element is provided to be penetrated by a number (or plurality) of electrical contacts of the male plug connector (contact pins). Especially, the sterility separation element may be provided to form an intermediate layer between the female plug connector/plug socket and the male plug connector (contact pin) during the plugging process thereof.

In an advantageous embodiment (alternatively or cumulatively), the sterility separation element may be dimensioned such that the flat element, when in use, forms a cuff over one of the plug connectors. This allows the plug connector to be easily grasped without the risk of contamination.

The sterility separation element may, for example, (alternatively or cumulatively) be impregnated with a disinfectant. For example, the disinfectant may be produced based on alcohol (ethanol or 2-propanol) and mecetronium ethylsulfate. Additionally, the disinfectant may comprise a refatting substance so as not to cause skin irritation. Thus, the flat element may be a hand disinfectant wipe. The disinfectant may also comprise one or more of the following: oxidizing agents, peracetic acid, hydrogen peroxide, halogens (iodine, chlorine compounds), ozone, phenol derivatives (including chloroxylenol, triclosan), aldehydes (e.g. formaldehyde), alcohols, detergents, nitrogen compounds (e.g. benzalkonium chloride) and the like (chlorhexidine, octenidine, polyhexanide). Thus, the flat element itself may be sterile/germ-free.

Likewise, the sterility separation element may preferably (alternatively or cumulatively) be configured to form, in use, the cuff up to a cable connected to the plug connector. This may enable personnel to easily operate/connect the plug connector without them becoming contaminated.

According to any or more embodiments, the sterility separation element may be a foil, a drape or a sheet. Therein, the sterility separation element may be configured tear-resistant. At least, the flat element may sustain a predetermined tensile force, for example at least 1 $N/mm^2$ or 10 $N/mm^2$, i.e. be resistant to tensile forces. The flat element may also be configured for a maximum tensile force, for example 15 $N/mm^2$ or 150 $N/mm^2$.

Especially, the non-sterile plug connector may (alternatively or cumulatively) include a mount for attachment to an external stationary object such as an operating table. This can enable personnel to only have to touch sterile parts to connect the sterile and non-sterile cables, for example by means of the plug connection adapter or by means of the flat element.

BRIEF DESCRIPTION OF THE DRAWING FIGURES

The disclosure is explained in more detail below based on a preferred embodiment with reference to the accompanying figures as follows.

Figure 3:
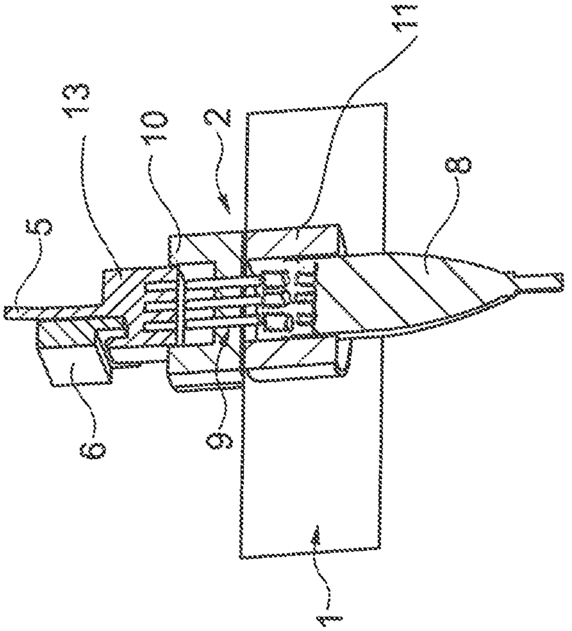
Figure 4:
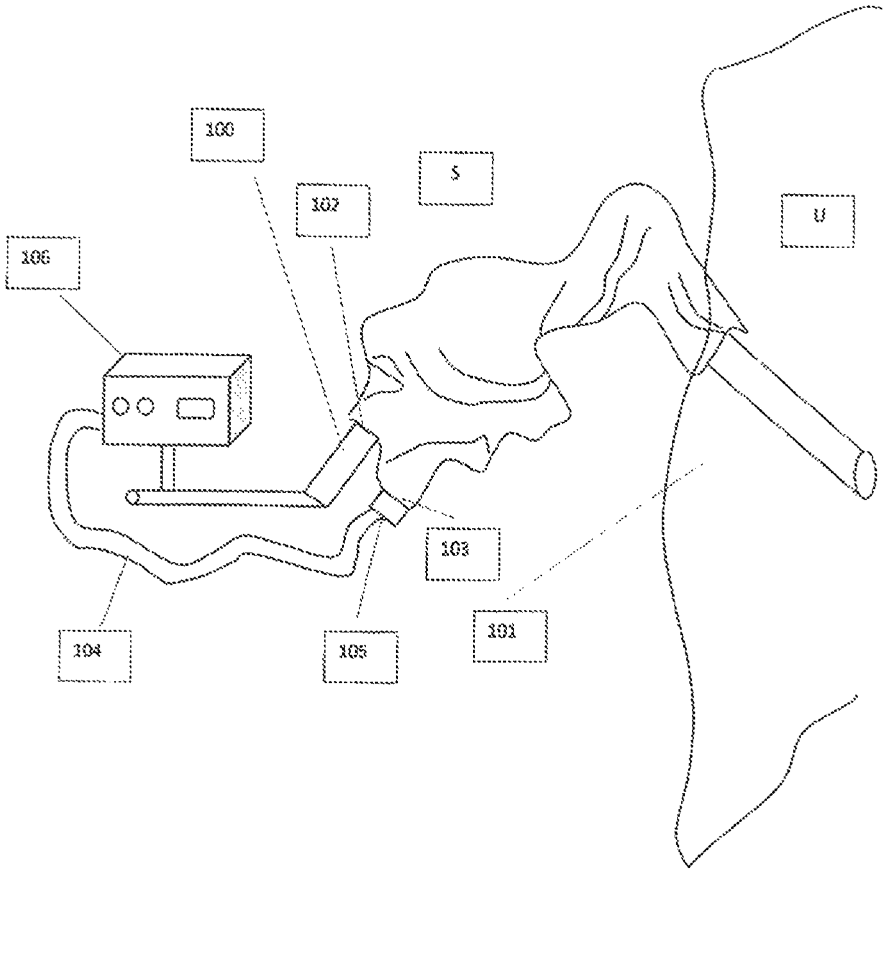

FIG. 3 shows a schematic illustration of a sterility barrier in form of a sterility separation element with the electro-mechanical lock according to a second preferred embodiment of the present disclosure (with regard to the at least one electrical contact pin having two free pin ends), especially configured as a sterility separation module; and FIG. 4 shows a general arrangement/division of a sterile and non-sterile area.

DETAILED DESCRIPTION

Figure 1:
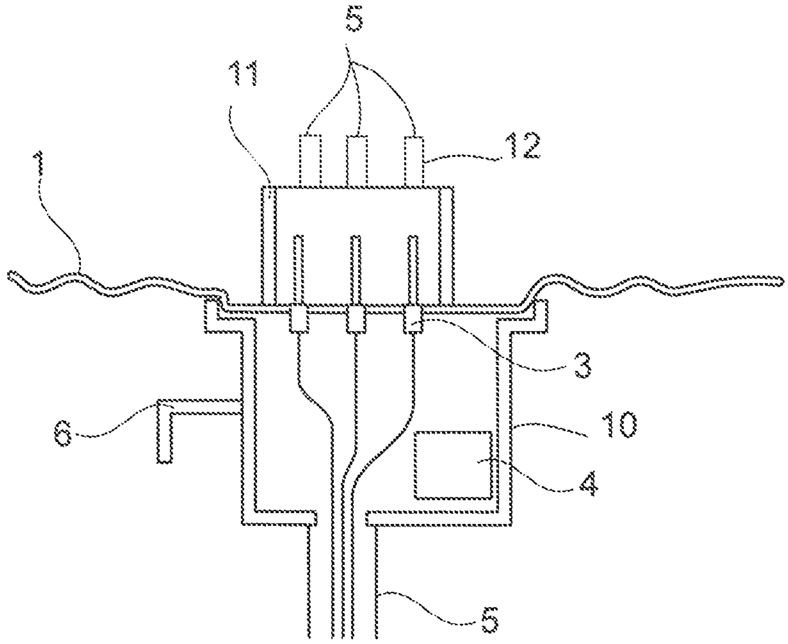
FIG. 1 shows a schematic illustration of a sterility barrier in form of a sterility separation element with an electro-mechanical lock in general illustration or, respectively, in a general basic structure for illustrating essential parts/components of an arrangement according to the disclosure.

FIG. 1 shows a sterility barrier in general illustration or, respectively, in a general basic structure for illustrating essential parts/components of an arrangement according to the disclosure, the arrangement having:

- a flexible, preferably drape- or sheet-like sterility separation element 1 (hereinafter referred to simply as sterility drape);
- an electro-mechanical lock 2 in/at the sterility drape 1, having at least one electrical contact pin 9 which individually penetrates the sterility separation element 1; and
- a (first) line bus 5, consisting of a number/plurality of lines/cables, which leads to the lock 2 in a non-sterile area, and a further (second) line bus 5, consisting of a corresponding number/plurality of lines/cables, which leads away from the lock 2 in the sterile area.

Specifically, the sterility drape 1 is a germ-tight fabric or a (germ-tight) foil that is provided and configured to separate a sterile area from a non-sterile area. For example, the sterile area may be an operating area/room in which a robot arm or various drive and/or control devices/medical devices are located, which in themselves constitute non-sterile areas and must therefore be isolated from the sterile area in a germ-tight manner. For this purpose, such non-sterile areas may be surrounded/sheathed by the sterility drape 1 shown, wherein it must however be ensured that, for example, electrical devices, energy sources or control systems within the non-sterile area have electrical contact through the sterility drape 1 to (medical technology or, respectively, surgical) devices, such as surgical electromotive handles, lighting means, etc. in the sterile area, without the germ-tight sterility barrier being damaged/disrupted.

This basic structure or general basic structure corresponds to the arrangement that is shown in FIG. 4, so that in relation thereto reference can be made to the above description with reference to FIG. 1. For the purpose of the maintenance of the sterility, the electro-mechanical lock 2 according to the disclosure is provided, as described in more detail below.

In principle, the electro-mechanical lock 2 according to the present disclosure has a number, preferably a plurality, of contact pins (lock contacts) 9, which are preferably supported/fixed in a first housing (sleeve) 10 such that they project from the first housing 10 in form of a mandrel on one housing side (hereinafter referred to as the abutment side). The contact pins 9 are arranged at a parallel distance from one another.

Each contact pin 9 has at least one free/freely projecting pin end or, respectively, free end section which is provided and configured/adapted to pierce the sterility drape 1. For this purpose, the one pin end of the corresponding contact pin 9 may, for example, be pointed or sharpened, or the respective contact pin 9 has such a small diameter that it can be pierced through the sterility drape 1 without the sterility drape 1 tearing. The decisive factor here is that a very narrow piercing hole is formed so that the pierced contact pin 9 is subsequently surrounded by the sterility drape 1 fitting over its entire circumference in a germ-tight manner.

Preferably, control electronics may be located already within the first housing 10, for example electronics 4 for controlling the battery of an electrical medical technology/surgical device located within the sterile area or of similar work equipment. In this case, each electrical medical technology/surgical device within the sterile area is assigned a device-specific lock 2, for example with device-specific control elements or power supplies or the like already within the first lock housing 10.

According to the further disclosed partial aspect as shown in FIG. 1, the at least one electrical contact pin 9 has a free pin end that is provided and configured to come into electro-mechanical or electroconductive plug contact with a corresponding electrical plug socket 12 of the at least one line 5 on the sterile or non-sterile side of the sterility separation element 1, whereas at the other pin end the at least other line 5 is firmly connected on the correspondingly other side of the sterility separation element 1. Thereby, a line (cable) is fixed to the other free pin end or, respectively, the other free end section of each contact pin 9, which are combined to form a line bus (cable harness) 5, which is led to the outside through a housing opening at a housing side facing away from the abutment side. This cable harness 5 is then electrically coupled within the sterile area to a corresponding medical device (not further shown).

Finally, in general (as shown in FIG. 1), a holder 6 may be arranged/configured at the first housing 10, with which the first housing 10 can be fixed to a (stationary) fixed object, for example an operating table, such as to stationarily hold the lock 2 and also the sterility drape 1.

On the side of the sterility drape 1 facing away from the first housing 10, a second housing 11 is shown which has a substantially hollow cylindrical/tubular shape, wherein one end face thereof abuts to the sterility drape, and wherein the sterility drape 1 is sandwiched between the first 10 and the second housing 11. Thereby, the one free pin ends/end sections of the contact pins 9 (which have already been pressed through the sterility drape 1) project into the interior of the hollow cylindrical second housing 11.

These free pin ends of the contact pins 9 are provided and configured to come into electrical plug contact with contact sockets 12, to which also lines/cables are attached, which are brought together to form a cable harness 5 comparable to the cable harness 5 on the other sterility drape side. As soon as these plug sockets 12 are plugged onto the free pin ends/end sections of the contact pins 9, they press the sterility drape 1 against the abutment side of the first housing 10 located on the other sterility drape side and thus hold the entire lock assembly together.

At this point, it should be noted that the contact sockets 12 shown individually in FIG. 1 may also be combined to form a plug whose shape is adapted to the hollow cylindrical second housing 12 so that it can be plugged into this.

Figure 2:
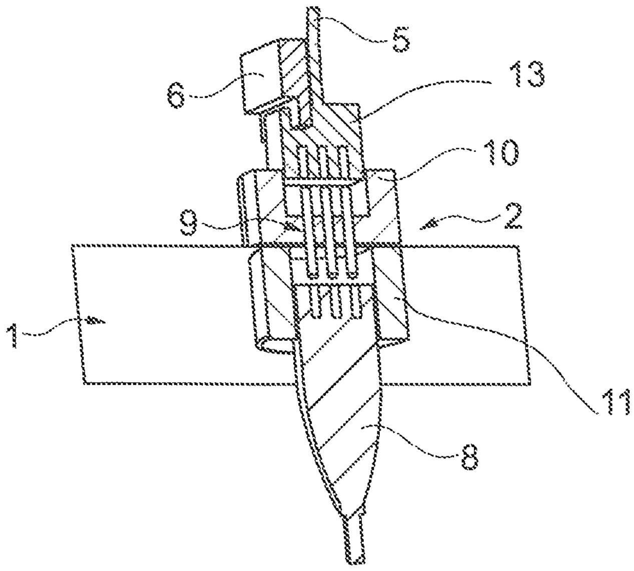
FIG. 2 shows a schematic illustration of a sterility barrier in form of a sterility separation element with the electro-mechanical lock according to a first preferred embodiment of the present disclosure (with regard to the at least one electrical contact pin having two free pin ends), especially configured as a sterility separation module.

FIG. 2 shows a first embodiment of the present disclosure, whereby in the following, essentially the design features different to the example according to FIG. 1 are discussed (all other above descriptions thus also apply to the first embodiment according to the disclosure); in this context, for the same components also the same terms and reference numerals are used.

In this case, the first housing 10 in contrast to the first housing 10 according to FIG. 1 (in accordance with the second housing 11) also forms an insertion shaft for a number of plug sockets or a plug 13, in which the plug sockets are combined and which is adapted to the insertion shaft of the first housing 10. That is, in the first embodiment according to the disclosure (or, respectively, the modification) according to FIG. 2, the fixed line connections 3 as shown in FIG. 1 are replaced by a further plug connection, so that the contact pins 9 in this case have two free pin ends/end sections which are provided and configured for a plug connection with corresponding lines/cables.

Furthermore, in the first embodiment according to the disclosure according to FIG. 2, the holder 6 for fixing the lock 2 to a (stationary) fixed object is not arranged/configured at the first housing 10, but at the plug 13. For that matter, in the first embodiment according to the disclosure in accordance with FIG. 2, that plug 8 is now also illustrated graphically, as it was previously mentioned as a replacement/alternative for the plug sockets 12 shown in FIG. 1.

In summary, the disclosure relates to a sterility separation element 1 for sterility separation, which is provided to be arranged between plus connectors 10, 11 of a plug connection/electro-mechanical lock and thus to provide sterility separation of the plug connectors 10, 11.

In FIG. 3, a second embodiment of the present disclosure is shown at least schematically, with only the differences from the first embodiment being described more specifically below.

As can be seen in FIG. 2, the contact pins 9 are configured as uniform rods which form insertion ends on both sides of the sterility separation element 1 which are insertable in the manner of a plug into insertion sockets in the manner of a socket. This means that sockets must be provided on both sides of the sterility separation element 1 which can be brought into contact engagement with plugs of the electrical/electro-mechanical lock 2 which are configured on both sides.

However, it has been shown that medical electrical instruments are already equipped with electrical cables at which plugs with simple contact pins are usually already mounted. In order to connect these to the lock 2 according to FIG. 2, an additional adapter would have to be provided. In order to avoid such an additional component, it is provided in the second embodiment of the disclosure that, at least on the sterile side of the sterility separation element 1, the at least one contact pin 9 is configured in form of a sleeve/plug socket at the end, such that the lock 2 on the sterile side of the sterility separation element 1 forms a type of socket into which a plug with at least a single, simple contact pin is insertable then, as shown for example in FIG. 1. This variant has the advantage over the variant according to FIG. 2 that a plug already present on the medical instrument can be brought directly into plug contact with the lock 2.

According to the further partial aspect of the disclosure, especially with reference to the schematic illustration of FIG. 1 (especially with regard to the feature of the at least one electrical contact pin having a free pin end and another pin end firmly connected to a respective line), which is not the subject matter of this present application but may be prosecuted in a later divisional application, the object is (alternatively) solved by the following features or, respectively, combination of features:

1st embodiment according to the further partial aspect: Sterility barrier with a flat sterility separation element 1, preferably in form of a covering or separation sheet, and an electro-mechanical lock 2, which is integrated or insertable/positionable in the sterility separation element 1, for the electrical connection of at least one electrical line 5 on the one, non-sterile side of the sterility separation element 1 to at least one electrical line 5 on the other, sterile side of the sterility separation element 1, the electro-mechanical lock 2 having at least one electrical contact pin 9 which individually penetrates the sterility separation element 1, such that the sterility separation element 1 fits over its entire circumference in a germ-tight manner directly to the at least one electrical contact pin 9; where the at least one electrical contact pin 9 has a freely projecting pin end which is provided and configured to come into electro-mechanical or electroconductive plug contact with a corresponding electrical plug socket and/or an electrical pin 12 of the at least one line 5 on the sterile or non-sterile side of the sterility separation element 1, whereas on the other pin end the at least other line 5 is firmly connected on the corresponding other side of the sterility separation element 1.

2nd embodiment according to the further partial aspect: Sterility barrier according to the 1st embodiment according to the further partial aspect, where the sterility separation element 1 is foil-, drape- and/or plate-like.

3rd embodiment according to the further partial aspect: Sterility barrier according to any of the preceding 1st or 2nd embodiments according to the further partial aspect, where the electro-mechanical lock 2 forms an electro-mechanical coupling module with at least one first module housing 10 having a sterility separation element abutment side or abutment surface from which the one free pin end of the at least one electrical contact pin 9 projects freely.

4th embodiment according to the further partial aspect: Sterility barrier according to the 3rd embodiment according to the further partial aspect, where the first housing is closed on the housing side facing away from the abutment side, with a passage opening for the at least one line 5 on the sterile or non-sterile side of the sterility separation element 1, that is firmly connected to the at least one contact pin 9.

5th embodiment according to the further partial aspect: Sterility barrier according to any of the preceding 3rd to 4th embodiments according to the further partial aspect, where the electro-mechanical coupling module has a second module housing 11 in form of a hollow cylinder which encloses an axially continuous insertion shaft and which is provided and configured to be abutted to the sterility separation element 1 on one end face such that the free end of the at least one contact pin 9, that has already penetrated the sterility separation element 1, projects into the insertion shaft of the second module housing 11, wherein, on the other end face, the plug socket 12 of the at least one other line 5 is insertable.

6th embodiment according to the further partial aspect: Sterility barrier according to any of the preceding 1st to 5th embodiments according to the further partial aspect, where a plurality of contact pins 9 is provided which are spaced apart in parallel, wherein a corresponding number of contact sockets 12 is provided on at least one side of the sterility separation element 1, which are combined to form a single plug 8, 13.

7th embodiment according to the further partial aspect: Sterility barrier according to the 6th embodiment according to the further partial aspect, where the first module housing 10 or the plug 13 is configured or equippable with a holder 6 which is provided and configured to be fixed to an external object, especially an operating table.

The invention claimed is:

1. A sterility barrier system comprising:
a sterility separation element; and
an electro-mechanical lock that is integrated or insertable/positionable in the sterility separation element to electrically connect a first electrical line on a non-sterile side of the sterility separation element to a second electrical line on a sterile side of the sterility separation element,
the electro-mechanical lock comprising at least one electrical contact pin configured to penetrate the sterility separation element,
the at least one electrical contact pin comprising a first pin end and a second pin end that each are freely projecting and configured to come into electro-mechanical or electroconductive plug contact with corresponding electrical pins and/or plug sockets of the first electrical line and the second electrical line, respectively;
wherein the at least one electrical contact pin individually penetrates the sterility separation element such that the sterility separation element fits directly to the at least one electrical contact pin over its entire circumference in a germ-tight manner.

2. The sterility barrier system according to claim 1, wherein the sterility separation element comprises a foil, a drape, or a plate.

3. The sterility barrier system according to claim 1, wherein the electro-mechanical lock forms an electro-mechanical coupling module with a first module housing having an abutment side or abutment surface from which the first pin end projects freely.

4. The sterility barrier system according to claim 3, wherein the first module housing forms an insertion shaft on a housing side facing away from the abutment side or abutment surface, the second pin end projecting into the insertion shaft, with at least one plug socket of the first electrical line or the second electrical line being insertable into the insertion shaft.

5. The sterility barrier system according to claim 3,
wherein the sterility separation element comprises a first end face and a second end face,
wherein the electro-mechanical coupling module comprises a second module housing comprising a hollow cylinder that encloses an insertion shaft that is axially continuous and configured to be abutted to the sterility separation element on the first end face such that one of the first pin end and the second pin end of the at least one electrical contact pin projects into the insertion shaft of the second module housing, and
wherein, on the second end face, a plug socket of the second electrical line is insertable.

6. The sterility barrier system according to claim 3,
wherein the at least one electrical contact pin comprises a plurality of contact pins that are spaced apart in parallel, and
wherein at least one of the sterile side and the non-sterile side of the sterility separation element comprises a plurality of contact sockets corresponding to the plurality of contact pins, which are combined to form a plug.

7. The sterility barrier system according to claim 6, wherein the first module housing or the plug is configured or equippable with a holder configured to be fixed to an external object.

8. The sterility barrier system according to claim 1, wherein the first pin end and the second pin end, or sections of the first pin end and the second pin end, form a male plug configured and adapted to be connected to a female plug socket of a cable, wherein the male plug is complementary to the female plug socket.

9. The sterility barrier system according to claim 1, wherein the first pin end and the second pin end, or sections of the first pin end and the second pin end, form a female plug socket configured to be connected to a male plug of a cable.

10. A system comprising:
the sterility barrier system according to claim 1;
a medical instrument; and
an energy source for the medical instrument,
wherein the electro-mechanical lock comprises an intermediate plug between the medical instrument and the energy source.

11. A sterility barrier system comprising:
a sterility separation element; and
an electro-mechanical lock that is integrated or insertable/positionable in the sterility separation element to electrically connect a first electrical line on a non-sterile side of the sterility separation element to a second electrical line on a sterile side of the sterility separation element,
the electro-mechanical lock comprising at least one electrical contact pin configured to penetrate the sterility separation element,
the at least one electrical contact pin having a first pin end and a second pin end,
the first pin end freely projecting and configured to come into electro-mechanical or electroconductive plug contact with a corresponding electrical plug socket and/or an electrical pin on the first electrical line, and the second pin end being firmly connected to the second electrical line;

wherein the at least one electrical contact pin individually penetrates the sterility separation element such that the sterility separation element fits directly to the at least one electrical contact pin over its entire circumference in a germ-tight manner.

12. The sterility barrier system according to claim 11, wherein the electro-mechanical lock forms an electro-mechanical coupling module with a first module housing having a sterility separation element abutment side or abutment surface from which the first pin end projects freely.

13. The sterility barrier system according to claim 12, wherein the first module housing is closed on a housing side facing away from the sterility separation element abutment side or abutment surface, with a passage opening for the first electrical line or the second electrical line to freely extend beyond and outside the otherwise closed first module housing in an extending direction away from the sterility separation element abutment side or abutment surface.

14. The sterility barrier system according to claim 12, wherein the sterility separation element comprises a first end face and a second end face, wherein the electro-mechanical coupling module has a second module housing comprising a hollow cylinder that encloses an insertion shaft that is axially continuous and configured to be abutted to the sterility separation element on the first end face such that one of the first pin end and the second pin end of the at least one electrical contact pin projects into the insertion shaft, and wherein, on the second end face, a plug socket of the second electrical line is insertable.

15. The sterility barrier system according to claim 11, wherein the at least one electrical contact pin comprises a plurality of contact pins that are spaced apart in parallel, wherein at least one of the sterile side and the non-sterile side of the sterility separation element comprises a plurality of contact sockets corresponding to the plurality of contact pins, which are combined to form a plug.

16. A sterility barrier electro-mechanical lock system that is securable to a sterility separation element at an abutment region of the sterility separation element, and is configured to electrically connect a first electrical line on a first side of the sterility separation element with a second electrical line on a second side of the sterility separation element, the second side being opposite the first side, wherein the sterility barrier electro-mechanical lock system comprises:

a first module comprising a closed first module abutment surface configured to abut the first side of the sterility separation element at the abutment region, a first module receptacle extending away from the closed first module abutment surface, and one or more electrical contact pins, each electrical contact pin having:

a front pin end freely projecting from the closed first module abutment surface and configured to individually penetrate the sterility separation element, from the first side and through the abutment region, such that the sterility separation element fits directly to the electrical contact pin over an entire circumference of the electrical contact pin in a germ-tight manner, and a rear pin end freely projecting into the first module receptacle from a bottom surface of the first module receptacle located opposite the closed first module abutment surface;

a first plug comprising the first electrical line, the first plug being configured to be inserted into the first module receptacle to electrically connect the first electrical line to the rear pin end of each of the one or more electrical contact pins;

a second module formed in an open tube shape defining a second module receptacle, wherein a solid outer peripheral end face of the open tube shape defines a second module abutment surface configured to abut to the second side of the sterility separation element at the abutment region, such that, when assembled, an axial direction of the second module extends in axial continuity with an axial direction of the first module across the sterility separation element, and the front pin end of each of the one or more electrical contact pins projects freely into the second module receptacle; and a second plug comprising the second electrical line, the second plug being configured to be inserted into the second module receptacle to electrically connect the second electrical line to the front pin end of each of the one or more electrical contact pins.

17. The sterility barrier electro-mechanical lock system according to claim 16, wherein the front pin end of each of the one or more electrical contact pins is configured to be electrically connected with the second electrical line by insertion into a corresponding male plug socket of the second plug.

18. The sterility barrier electro-mechanical lock system according to claim 16, wherein the first side of the sterility separation element is a non-sterile side thereof, and the second side of the sterility separation element is a sterile side thereof.

19. The sterility barrier electro-mechanical lock system according to claim 16, wherein the first module or the first plug is configured or equippable with a holder configured to be fixed to an external object.

20. A modular sterility barrier system comprising:

the sterility barrier electro-mechanical lock system according to claim 16; and the sterility separation element.

* * * * *